United States Patent
Huan et al.

(12) 
(10) Patent No.: US 6,696,246 B1
(45) Date of Patent: Feb. 24, 2004

(54) ASSAYS USING CROSSLINKABLE IMMOBILIZED NUCLEIC ACIDS

(75) Inventors: Bingfang Huan, Cupertino, CA (US); David Albagli, Menlo Park, CA (US); Michael L. Wood, Mountian View, CA (US); Reuel B. Van Atta, Mountain View, CA (US); Peter C. Cheng, San Jose, CA (US)

(73) Assignee: Naxcor, Inc., Menlo Park, CA (US)

( * ) Notice: Subject to any disclaimer, the term of this patent is extended or adjusted under 35 U.S.C. 154(b) by 0 days.

(21) Appl. No.: 09/379,888

(22) Filed: Aug. 23, 1999

Related U.S. Application Data (63) Continuation-in-part of application No. 09/138,195, filed on Aug. 21, 1998, now abandoned.

(51) Int. Cl.$^7$ .......................... C12Q 1/68; C12P 19/34; C07H 21/02; C07H 21/04; C07H 19/00
(52) U.S. Cl. ..................... 435/6; 435/91.1; 435/91.2; 536/22.1; 536/23.1; 536/24.3; 536/24.31; 536/24.32; 536/24.33
(58) Field of Search ................ 435/6, 91.1, 91.2; 536/22.1, 23.1, 24.3, 24.31, 24.32, 24.33; 436/518

(56) References Cited

U.S. PATENT DOCUMENTS

| | | | |
|---|---|---|---|
| 4,599,303 A | 7/1986 | Yabusaki et al. | 435/6 |
| 4,826,967 A | 5/1989 | Glass | 536/23 |
| 4,886,741 A | 12/1989 | Schwartz | 435/5 |
| 5,028,594 A | 7/1991 | Carson | 514/23 |
| 5,082,934 A | 1/1992 | Saba et al. | 536/17.6 |
| 5,225,326 A | 7/1993 | Bresser et al. | 435/6 |
| 5,346,811 A | 9/1994 | Galindo-Castro et al. | 435/5 |
| 5,487,970 A | 1/1996 | Rowley et al. | 435/6 |
| 5,492,806 A | 2/1996 | Drmanac et al. | 435/5 |
| 5,521,061 A | 5/1996 | Bresser et al. | 435/5 |
| 5,525,464 A | 6/1996 | Drmanac et al. | 435/6 |
| 5,616,464 A | 4/1997 | Albagli et al. | 435/6 |
| 5,645,993 A * | 7/1997 | Chance et al. | 435/6 |
| 5,652,096 A * | 7/1997 | Cimino et al. | 435/6 |
| 5,665,540 A | 9/1997 | Lebo | 435/6 |
| 5,695,940 A | 12/1997 | Drmanac et al. | 435/6 |
| 5,700,637 A | 12/1997 | Southern | 435/6 |
| 5,707,801 A | 1/1998 | Bresser et al. | 435/6 |
| 5,719,023 A | 2/1998 | Zarling et al. | 435/6 |
| 5,721,098 A | 2/1998 | Pinkel et al. | 435/6 |
| 5,723,320 A | 3/1998 | Dehlinger | 435/91.1 |
| 5,744,305 A | 4/1998 | Fodor et al. | 435/6 |
| 5,750,340 A | 5/1998 | Kim et al. | 435/6 |
| 5,767,259 A | 6/1998 | Albagli et al. | 536/23.1 |
| 5,770,722 A | 6/1998 | Lockhart et al. | 536/25.3 |
| 5,849,486 A * | 12/1998 | Heller et al. | 435/6 |

FOREIGN PATENT DOCUMENTS

| | | |
|---|---|---|
| DE | 3804243A 1 | 8/1989 |
| EP | 0 130 532 A2 | 1/1985 |
| EP | 0 324 616 A2 | 7/1989 |
| WO | WO 90/01563 | 2/1990 |
| WO | WO 90/08838 | 8/1990 |
| WO | WO 90/12020 | 10/1990 |
| WO | WO 93/16095 | 8/1993 |
| WO | WO 94/24120 | 10/1994 |
| WO | WO 96/20289 | 7/1996 |
| WO | WO 96/28438 | 9/1996 |
| WO | WO 96/34984 | 11/1996 |

OTHER PUBLICATIONS

Watson et al Recombinant DNA 2nd edition 1992 pp. 127–130.*
Southern, "Detection of specific sequences among DNA fragments separated by gel electrophoresis," *J. Mol. Biol.*, 98:503–517 (1975).
Zehnder et al., "Cross–linking hybridization assay for direct detection of factor V Leiden mutation," *Clinical Chemistry*, 43:1703–1708 (1997).

* cited by examiner

*Primary Examiner*—Jeffrey Siew
(74) *Attorney, Agent, or Firm*—Ralph T. Lilore

(57) ABSTRACT

Improved methods for in situ hybridization assays of cellular and subcellular systems and tissue sections, and immobilization-based assay techniques such as Northern blotting, Southern blotting, dot blots, and the like, and assay techniques wherein the probes are bound to substrates are disclosed. The subject invention employs crosslinker-containing hybridization probes capable of forming covalent bonds between the probe and the target nucleic acid. Upon activation, the crosslinker will, if the probe has hybridized with its essentially complementary target, form covalent bonds with the complementary strand to covalently crosslink the probe to the target. Subsequently, stringent wash conditions may be employed to reduce background signals due to non-specific absorption or probes or targets, while retaining all crosslinked probe/target hybrids. Also disclosed are diagnostic kits for use in clinical and diagnostic laboratories.

16 Claims, 1 Drawing Sheet

(1 of 1 Drawing Sheet(s) Filed in Color)

Figure 1A
CaSki cells, with crosslinking

Figure 1B
CaSki cells, without crosslinking

Figure 1C
C-33 cells, with crosslinking

ASSAYS USING CROSSLINKABLE IMMOBILIZED NUCLEIC ACIDS

CROSS REFERENCE TO RELATED APPLICATIONS

This application is a continuation-in-part of U.S. Ser. No. 09/138,195, filed Aug. 21, 1998 abandoned, the disclosure of which is incorporated by reference herein.

BACKGROUND OF THE INVENTION a) Field of the Invention

This invention relates generally to methods of detecting nucleic acid sequences using oligonucleotide probes or arrays of probes that have a crosslinking moiety in assays where either the probe or the target molecule is bound to a solid support. The surface-bound DNA or RNA may be immobilized cellular or subcellular systems, or immobilized arrays of DNA or RNA preparations.

b) Description of Related Art

Numerous useful techniques in the biological sciences involve the immobilization of biological material on a solid support of some kind. Immobilized nucleic acid hybridization assays constitute an important class of these methods. Examples of nucleic acid-based assays where the sample being assayed is immobilized include in situ hybridization and blotting assays. Examples of assays where the sample is contacted with immobilized probes include gene chip technologies.

In situ hybridization techniques are a valuable method for identifying the presence of specific nucleic acid sequences within cellular or subcellular systems. Unlike in vitro techniques in which the nucleic acids of interest are retained in some manner while the remainder of the sample is degraded in order to perform the assay measurement, in situ techniques allow one to assay for the presence of specific sequences among substantially intact cellular or subcellular structures.

In blotting assays, DNA or RNA bound to a membrane (or filter paper), in many cases after having been migrated through a gel, is probed for the presence of a specific nucleic acid sequence. Immobilization techniques for DNA assays were first demonstrated by Southern, *J. Mol. Biol.*, 1975, 98, 503. Since then many derivative procedures have been developed. These derivative procedures include Northern blot techniques in which RNA is immobilized and assayed via hybridization and dot blot techniques where a solution containing nucleic acid molecules is directly immobilized on the membrane or filter and assayed via hybridization.

In immobilized nucleic acid-based assays, oligonucleotide probes are contacted with the immobilized sample, or a sample is contacted with immobilized probes, and evidence that the probe has hybridized with its essentially complementary sequence is determined by development of a signal from a direct or an indirect reporter system.

Achieving a desirable signal-to-noise ratio is a major challenge of immobilized nucleic acid hybridization assays. In situ PCR is one method that has been attempted for improving the sensitivity of in situ assays. In this technique, cellular, subcellular, or tissue samples are prepared and primer pairs are introduced. The samples are then subjected to repeated thermal cycles in the same manner that PCR is typically carried out. It is expected that if the target sequence is present then copies of the PCR amplicons will be amplified. However, significant problems with the in situ PCR technique remain.

In addition to the problems encountered for solution-based PCR such as enzyme inhibition, false priming, and primer dimerization, there are other issues specific to the in situ technique that contribute to inconsistent assay results:

1. The extent of cell permeabilization. If the pore size is too small then polymerase enzymes may not be able to enter the cell. If the pore size is too large then the amplicon may freely leave the cell. These effects may be variable within one sample as well as from sample to sample.
2. Endogeneous inhibitors. Whereas for solution-based PCR assays a purpose of sample preparation procedures is to isolate the nucleic acids and remove enzyme inhibitors, in situ assays are necessarily performed within a cellular or subcellular environment and limit the possibilities for removing inhibitors.
3. Loss of amplicon. The permeabilized membranes may permit the amplicon to leave the cell during wash steps subsequent to the amplification reaction. It may also allow amplicons that have been washed out of adjacent cells to enter, leading to signal being observed in cells that did not originally contain the target.
4. Diffuse signals. The amplicons are not localized at the site of the target sequence, unlike probes that hybridize to the target. The amplicons freely move through the sample and may thus generate a diffuse signal that may be difficult to detect and not permit localization of the sequence being assayed. Together, the above factors account for some of the reasons for inconsistent results obtained by in situ PCR assays.

There is a recognized need to improve the detection sensitivity of probe-based hybridization assays for detection of immobilized nucleic acids. For example, methods to improve the rates of hybridization through the use of volume exclusion agents (U.S. Pat. No. 4,886,741) or increased probe concentrations (U.S. Pat. No. 5,707,801) have been disclosed. In U.S. Pat. No. 5,521,061, Bresser et al. describe the use of permeation enhancers and signal enhancers as a means to increase the sensitivity.

Previous disclosures indicate the need for improved methods for assays of immobilized nucleic acids, particularly in in situ hybridization assays.

The use of long probes (200 to 500,000 nucleotides in length) in these assays requires long hybridization times and contributes heavily to high background signals, because of countless opportunities for undesired, non-specific binding interactions provided by the additional sequence. However, long probes provide the advantage of being able to contain many reporter groups and thus provide stronger signals. Shorter probes (less than 200 nucleotides) offer the advantage of reduced hybridization times, but shorter probes are more susceptible to being washed away, thereby reducing the signal. Shorter probes also have the advantage of being prepared by automated synthesis procedures, but their use is limited in many types of assays because of the loss of hybridized probes during the critical washing steps.

Crosslinker-containing probes have been previously used in in vitro hybridization techniques (for instance, see U.S. Pat. No. 4,599,303, Yabusaki et al.). However, whether such probes are applicable to in situ hybridization or blotting techniques was not known. In in vitro techniques, the various biologic components have normally been chemically degraded by sample preparation steps, typical among which are boiling in alkaline solution, proteinase K treatment, and the like. In any event, the in vitro assays are typically designed to retain only the nucleic acid material on some solid support temporarily while removing the other components through removal of the supernatant solution in a series of wash steps. The hybridization step itself is usually performed in solution. If there should be nonspecific interaction between a probe and non-nucleic acid and biological components, this would not contribute to a false signal because these components are not retained in the assay.

However, in techniques in which the target DNA or RNA is immobilized during the hybridization step, especially in the presence of other biological components, non-specific interactions between the crosslinker-containing probes and any of these materials, including the solid support on which the target DNA or RNA is immobilized, would be disastrous to the outcome of the assay. Non-specific interactions between the crosslinker-containing probes and solid support material on which the biological sample is immobilized are of particular concern. For instance, positively-charged groups on a solid support material are helpful in the original immobilization of the target nucleic acid molecule, but they will also attract binding of the nucleic acid probe. Alternatively, exposed hydroxyl groups on the surface of a solid support material may form hydrogen bonds with the nucleic acid probe used. Crosslinker-containing probes are particularly problematic for non-specific binding, because they necessarily contain a highly reactive functional moiety. Although the intention is to use the crosslinking moiety to covalently attach the nucleic acid probe to the target nucleic acid, any crosslinker-containing probe which is non-specifically bound to the support or a non-target nucleic acid molecule could potentially become covalently attached, resulting in an excessively high background level.

In addition to the potentially problematic presence of biological material other than the target nucleic acid molecules, other aspects of the procedures used in hybridization protocols where the biological sample is immobilized can be detrimental to efforts to obtain a clear hybridization signal. For instance, in situ hybridization procedures employ the use of a fixative, a compound which kills the cell but preserves its morphology and/or nucleic acids for an extended period of time. However, these fixatives, while preserving structure, often reduce hybridization efficiency. Networks may be formed in the process, trapping nucleic acids and antigens and rendering them inaccessible to probes. Some fixatives also covalently modify nucleic acids, preventing later hybrid formation and decreasing signal.

Thus, there exists a need for immobilized nucleic acid hybridization assays with improved signal-to-noise ratios. However, the applicability of crosslinker-containing probes to these immobilized assays and their effectiveness in combating the signal-to-noise problem have been unclear.

The use of electric fields to direct the binding of charged biomolecules has been disclosed in U.S. Pat. Nos. 5,929,208; 5,605,662; 5,849,486; and 5,632,957. This technique suffers from transient binding of the probe to the target. Moreover, the application of electric-field induced stringent wash techniques suffers from having to use compromised conditions in the same way as buffered stringent washes because the probes are always subject to being washed away.

SUMMARY OF THE INVENTION

It is an object of the present invention to provide a method for assaying immobilized nucleic acid targets using crosslinker-containing probes to improve the sensitivity and the reproducibility of the assay.

It is a further object of the present invention to provide methods for assaying solutions of target nucleic acids using immobilized crosslinker-containing probes to improve the sensitivity and the reproducibility of the assay.

The sensitivity of an assay is determined by the signal-to-background ratio of the observable being measured. The reproducibility of an assay is determined by factors that influence the signal levels or the background levels. Variation of either of these levels will cause varying signal-to-background ratios and complicate the interpretation of the assay.

The present invention satisfies the need for improved methods of assaying immobilized nucleic acids. These methods provided by the invention offer the advantage of superior signal-to-background ratios compared to standard hybridization assay techniques.

The present invention provides for a method of determining the presence of a target nucleic acid molecule in a biological sample, wherein either the target molecule or the biological sample is immobilized. In this method, a nucleic acid probe having a crosslinking moiety capable of forming a covalent crosslink between the nucleic acid probe and the target nucleic acid is contacted with the biological sample so that hybridization between the target nucleic acid and the nucleic acid probe occurs. A covalent bond between the nucleic acid probe and the target nucleic acid molecule is then formed. At least one washing step follows to remove the excess or nonspecifically bound hybridization partner from the site of the biological sample. Stringent, denaturing conditions and washes may also optionally be used to remove any nucleic acid probe which is not covalently bound to a target nucleic acid. In a final step, the amount of crosslinked nucleic acid probe target complexes is determined.

In one embodiment, the biological sample is a cell, subcellular structure, body fluid, or tissue section. In another embodiment of the invention, the biological sample is a sample of nucleic acid molecules, preferably immobilized on nylon membrane or nitrocellulose paper.

The target nucleic acid molecule may be an animal, bacterial, fungal, human, parasitic, plant or viral nucleic acid.

In one embodiment of the invention, the crosslinking moiety of the labeled nucleic acid probe is selected from the group consisting of coumarins, furocoumarins, and benzodipyrones.

The formation of the covalent bond between the target nucleic acid and the nucleic acid probe may occur either photochemically or chemically.

In another embodiment, the present invention provides for an array, comprising a solid support and a plurality of different nucleic acid probes immobilized on the solid support, each nucleic acid probe having a base sequence essentially complementary to a defined region of a target nucleic acid molecule and having a crosslinking moiety capable of forming a covalent crosslink between the nucleic acid probe and the target nucleic acid molecule. The target nucleic acid molecule may be an animal, including human, bacterial, fungal, parastic, plant or viral nucleic acid. The crosslinking-moiety employed on the array is optionally selected from the group consisting of coumarins, furocoumarins, and benzodipyrones.

Methods for using arrays of probes for determining the presence of a plurality of target nucleic acid molecules in a biological sample are also provided.

Methods for using arrays for determining genotypes of particular sequences where several polymorphic sequences may be expected are also provided.

In alternative embodiments of the invention, methods for diagnosing a disease condition in a patient and kits useful in carrying out the methods of the invention are also provided.

BRIEF DESCRIPTION OF THE DRAWING

The file of this patent contains at least one drawing executed in color. Copies of this patent with color drawing (s) will be provided by the Patent and Trademark Office upon request and payment of the necessary fee.

DETAILED DESCRIPTION OF THE INVENTION

The present invention provides improved methods for performing immobilized nucleic acid hybridization assays. Examples of such assays include, but are not limited to, in situ hybridization, blotting assays, and the use of gene chips.

Nucleic acid hybridization is a process where two or more opposite strands of modified polynucleotides such as "PNA" (Nielson et al., U.S. Pat. No. 5,773,571) DNA, RNA, oligonucleotides, polynucleotides, or any combination thereof recognize one another and bind together through the formation of hydrogen bonds.

One embodiment of the invention provides for a method of determining the presence of a target nucleic acid molecule in a biological sample. This method involves first contacting a nucleic acid probe with the biological sample so that the nucleic acid probe can hybridize to the target nucleic acid molecule. The nucleic acid probe hybridized to the target nucleic acid molecule bears a crosslinking moiety capable of forming a covalent crosslink between the nucleic acid probe and the target nucleic acid molecule. The method also involves forming covalent crosslinks between the nucleic acid probe and the hybridized target nucleic acid molecule and washing to remove excess probe or target. A final step involves determining the amount of crosslinked nucleic acid probe target complexes.

The method for determining the presence of a target nucleic acid molecule in a biological sample may optionally comprise forming a covalent bond between the nucleic acid probe and the target nucleic acid molecule and subjecting the sample to stringent, denaturing conditions to remove non-covalently bound nucleic acid.

In one embodiment the biological sample is immobilized on a solid support. In another embodiment, the probe is immobilized on a solid support.

Typically, standard hybridization assays only allow for relatively gentle washings with salt buffers and the like. These washes are sufficient to remove nucleic acid probes which are not bound in any way to the biological sample. They are also sufficient to remove some of the probe molecules which are bound, but are bound only non-specifically (via limited hydrogen bonding and ionic interactions, for instance). The use of more stringent washes are problematic in these standard hybridization assays since they can cause denaturation of the critical duplex between the nucleic acid probe and the target nucleic acid molecule.

In the methods of the present invention, one or more stringent, denaturing washes may be performed. This invention provides for duplexes where the probe and target molecules are covalently linked to one another, not just hydrogen bonded together. Therefore, harsher conditions can be employed which will disrupt any undesirable, non-specific background binding, and even much or all of the hydrogen bonding between the target nucleic acid and the nucleic acid probe, but will not break the covalent bond linking the labeled probe to its target. For instance, washes with urea solutions or alkaline solutions may be used. Electric field-induced removal of non-crosslinking binding partners may be used. Heat may also be used. The covalent linkage therefore allows for a significant improvement in the signal-to-noise ratio of the assay.

The nucleic acid probe may consist of chemically synthesized or biologically prepared DNA or RNA polynucleotides from about 8 to about 200 bases in length or longer. The nucleic acid probe is preferably single-stranded. The nucleic acid probe has a base sequence which is essentially complementary to a defined region of its target nucleic acid molecule.

The crosslinking moiety can be directly incorporated into synthetic polynucleotides at the time of synthesis through the use of appropriately modified nucleoside or nucleotide derivatives. Alternatively, the crosslinking molecules can be introduced onto the probe through photochemical or chemical monoaddition. In some cases, the crosslinking moiety may be incorporated into a polynucleotide probe enzymatically by using an appropriately modified nucleotide or oligonucleotide which contains a cross-linking moiety.

The crosslinking moiety which is employed on the nucleic acid probe may be any chemical moiety which is capable of forming a covalent crosslink between the nucleic acid probe and the target nucleic acid molecule. For instance, the precursor to the crosslinking moiety can optionally be a coumarin, ftirocoumarin, or a benzodipyrone. Several of such crosslinkers useful in the present invention are known to those skilled in the art. For instance, U.S. Pat. Nos. 4,599,303 and 4,826,967 disclose crosslinking compounds based on furocoumarin suitable for use in the present invention. Also, in U.S. Pat. No. 5,082,934, Saba et al describe a photoactivatible nucleoside analogue comprising a coumarin moiety linked through its phenyl ring to a ribose or deoxyribose sugar moiety without an intervening base moiety. In addition, copending and commonly owned U.S. patent application Ser. No. 08/401,630 now U.S. Pat. No. 6,005,093 Dec. 21, 1995 discloses non-nucleosidic, stable, photoactive compounds that can be used as photo-crosslinking reagents in nucleic acid hybridization assays. These references, and all others referred to herein are incorporated by reference in their entirety.

The precursor of the crosslinking moiety may be a coumarin, 7-hydroxycoumarin, 6,7-dihydroxycoumarin, 6-alkoxy-7-hydroxycoumarin, psoralen, 8-methoxypsoralen, 5-methoxypsoralen, 4,5',8-trimethylpsoralen, 4'-hydroxymethyl-4,5',8-trimethylpsoralen, and 4'-aminomethyl-4,5',8-trimethylpsoralen, a haloalkyl coumarin, a haloalkyl furocoumarin, a haloalkyl benzodipyrone, or a derivative thereof. The moiety is incorporated into a nucleic acid sequence by methods taught in the above referred patents. Compounds containing fused coumarin-cinnoline ring systems are also appropriate for use in the present invention. In some embodiments, the cross-linking moiety may be part of a mono-adducted furocoumarin:nucleoside adduct.

The nature of the formation of the covalent bond comprising the crosslink will depend upon the crosslinking moiety chosen. In a preferred embodiment, the formation of the covalent bond occurs photochemically. In an alternative embodiment, the formation of the covalent bond occurs chemically.

The label on the nucleic acid probe can be attached to the crosslinking moiety directly. Alternatively, the label can be attached to another region of the probe. The label may be any molecule which can be detected. For instance, the label may be a radioactive nuclide, chromogenic, a chromophore, fluorogenic, a fluprophore, a chemiluminescent dye, an enzyme, or a ligand. Biotin-labeled nucleotides can be incorporated into DNA or RNA by nick translation, enzymatic, or chemical means. The biotinylated probes can be detected after hybridization using avidin/streptavidin, fluorescent, enzymatic or colloidal gold conjugates. Nucleic acids may also be labeled with other fluorescent compounds, with immunodetectable fluorescent derivatives or with biotin analogues. Nucleic acids may also be labeled by means of attaching a protein. Nucleic acids coupled or conjugated to radioactive or fluorescent histone H1, enzymes (alkaline phosphatase and peroxidases), or single-stranded binding (ssB) protein may also be used. Numerous such labeling methods are known to those skilled in the art.

Exemplary probe types and their associated detection methods include short (8–200 nt) probes with incorporated label and crosslinker, short probes with incorporated crosslinker and detection via in situ extension and concomitant label incorporation, and long (>200 nt) probes in which the crosslinker(s) is incorporated by use of crosslinker-containing primers, enzymatic incorporation of crosslinker-modified nucleotides, or enzymatic incorporation of crosslinker-containing oligonucleotides.

The target nucleic acid molecule in the assays of the present invention may be a DNA molecule or an RNA molecule. The target nucleic acid molecule may be an animal, bacterial, fungal, human, parasitic, plant or viral nucleic acid. The viral sequence may be from human papillomavirus, Epstein-Barr virus, or cytomegalovirus. However, many other possible targets exist and could be used in conjunction with the present invention. For instance, the target nucleic acid molecule may be of interest because it generates a selected gene product, is suspected of performing a critical cell-control function, is related to a repeat sequence, is suspected of containing a genetic defect which prevents expression of an active gene product, or may be related in chromosome position to a marker probe region with a known map position. Some applications of in situ hybridization assays include infectious disease testing (pathogen detection), cancer marker screening, mutation detection, tissue typing, gene profiling, analysis of trait incorporation, polymorphism genotyping, and assaying for antibiotic resistance genes.

In one embodiment of the invention, the biological sample is a cell, a subcellular system or structure, such as nuclei or mitochondria, a body fluid,.or a tissue section, and the method provides an improved procedure for in situ hybridization. In in situ hybridization procedures, cells or tissue sections which contain the target nucleic acid, typically chromosomal DNA or mRNA transcripts, are immobilized, and exposed to a solution of probes.

In one embodiment of the invention, the biological sample is a cell or tissue section collected from a patient. Cell samples that may be collected, immobilized, and used in the present invention are, for example, cervical cells (typically to test for human papillomavirus), buccal cells from the cheek (an easy source for chromosomal analyses), metaphase cells (for chromosomal spreads) or lymphocytes (to test for Epstein-Barr Virus or other viruses found in the lymphatic system). Tissue samples of interest may be tumor sections or biopsy specimens, which would typically be assayed for the presence of viruses or the expression of oncogenes or abnormal copy numbers of chromosomes.

Methods of fixing biological samples for in situ hybridization purposes are known to those skilled in the art. The cellular compartment and DNA structure may be fixed or permeabilized by treatment with an organic solvent and acid or bifunctional reagent to fix the structural components in their natural morphological relationship. Common fixatives include acetic acid, salts, methanol, formalin, paraformaledhyde, and glutaraldehyde. A tissue sample may be prepared for hybridization assays by first embedding the sample in wax or freezing the sample, followed by sectioning it into thin slices. The tissue section is then mounted on a slide and deparaffinized or thawed.

The biological material may also typically be treated with one or more of a number of agents capable of deproteinizing and/or delipidizing the structures. Such methods can involve the use of proteases, lipases, acid, organic solvents including alcohol, detergents or heat denaturation or combinations of these treatments. A common treatment involves one or more washes with methanol:acetic acid.

Subcellular structures, such as nuclei and mitochondria, can be prepared by conventional fractionation methods, such as isopycnic centrifugation, to obtain subcellular material in enriched or substantially purified form. Thereafter, the enriched structure preparation may be permeabilized and deproteinized as above and affixed to a slide by drying in preparation for probing.

In a preferred embodiment of the invention, the biological sample is affixed to a glass slide, typically by drying. The glass slide may be coated with a material to promote adhesion, such as, for example, poly-L-lysine. The biological sample may alternatively be immobilized on other types of support such as nylon or nitrocellulose.

Exemplary procedures for performing in situ hybridization using crosslinker-containing probes are detailed in Examples 1, 2, 3, and 4 below. The results of in situ hybridization experiments in which human papillomavirus was probed are described in Examples 2 and 4.

In an alternative embodiment of the invention, the biological sample is a sample of nucleic acid molecules. The sample of nucleic acid molecules may optionally be purified or semi-purified. The sample may comprise only nucleic acid molecules with a single sequence. In a preferred embodiment of the invention, however, the biological sample will comprise a mixture of many different nucleic acid molecules, the mixture being at least semi-purified from non-nucleic acid biological materials.

If the biological sample is a semi-purified or purified mixture of nucleic acid molecules, the sample is preferably immobilized on nylon membrane or nitrocellulose paper. In these embodiments, the hybridization assay is a modified blotting assay. In blotting assays, the DNA or RNA is bound to a membrane after having been migrated through a gel or is bound directly to the membrane, and then exposed to a solution of probes. There are three common nucleic acid-based blotting procedures in use: Southern blots, Northern blots, and dot blots.

Southern and Northern blotting procedures are useful for a variety of applications. In these techniques, the DNA (Southern) or RNA (Northern) is migrated through a gel to separate the nucleic acids into bands, after which a probe solution is contacted with the gel for hybridization. Information is obtained not only from simply observing in which band the probe/target hybrids are formed, but also from the position of those bands relative to other samples analyzed in the gel. Applications of Southern blots include mutation detection, restriction fragment length polymorphism (RFLP) analysis, DNA fingerprinting, and infectious disease detection. Northern blotting is a powerful tool for analyzing gene expression in cells. Densitometric analysis of the target band in the gel permits estimation of the level of gene expression. Furthermore, comparison of the length of the target RNA band with known standards allows for detection of incompletely processed or mutant species.

For Southern blots, the DNA is extracted from the sample by standard procedures. The DNA is digested with the restriction enzymes of choice, denatured, and the fragments obtained by these processes are separated through an agarose gel. The DNA is transferred to a nitrocellulose or nylon membrane by capillary elution, electroblotting, or vacuum transfer. Once the DNA is immobilized, the membrane is soaked in a solution of the crosslinker-containing probes and left to incubate to allow hybridization. The membrane is rinsed to remove excess hybridization solution and the probe-target hybrids are crosslinked for from about 5 to about 30 minutes, usually about 10 minutes, with light from a UV or visible source, depending upon the crosslinking moiety used. The membrane is washed, and the crosslinked probe/target hybrids are visualized either directly if, e.g., a fluorescent label has been incorporated into the probe, or after additional steps to incorporate, e.g. alkaline phosphatase to the crosslinked probes via ligand-receptor or antibody-antigen binding, and subsequent reaction of the bound enzyme with a substrate to produce a colored, luminescent, or chemiluminescent product.

For Northern blot applications, RNA is extracted from the sample under conditions that stabilize the RNA and inactivate endogenous RNase enzymes. The RNA is denatured with gentle heat and separated through an agarose gel. Thereafter, the procedure is essentially the same as for Southern blotting.

Dot blots are simple membrane-based procedures that concentrate the entire extracted nucleic acid sample in a small circular 'dot' on the membrane. The technique is useful for determining the presence or absence of a target sequence and can be adapted to quantitative applications by analyzing standards containing known target levels in parallel with the samples and quantifying the detection products with densitometric techniques. In addition, because each sample 'dot' occupies only a small area of the entire membrane, multiple samples can be assayed together.

Unlike a Southern or Northern blot, where the DNA/RNA fragments are separated through gels prior to transfer on to the membrane, no such step is required for a dot blot. After immobilization of the total sample on the membrane, labeled crosslinker-containing probes specific for the target sequence are hybridized and crosslinked to the target using the same procedures used for Southern and Northern blots. Detection of the crosslinked products is also done in the same way.

Another embodiment of the present invention provides for an improvement to a method for hybridizing a labeled nucleic acid probe to a target nucleic acid molecule in a biological sample. This improvement comprises using a nucleic acid probe having a crosslinking molecule capable of forming a covalent crosslink between the nucleic acid probe and the target single-stranded DNA and the additional step of forming covalent bonds between the nucleic acid probe and the target DNA molecule.

Still another embodiment of the invention provides an improvement to a method of hybridizing a nucleic acid probe to a target nucleic acid molecule immobilized on a substrate. The method involves using a nucleic acid probe having a crosslinking moiety capable of forming a covalent crosslink between the probe and the target, performing the step of forming the covalent crosslink, and thereafter applying an electric field across the substrate such that non-bound nucleic acid molecules will be repelled from the substrate and removed prior to the detection step.

Still another embodiment of the invention provides an improvement to a method of hybridizing a nucleic acid probe to a target nucleic acid molecule immobilized on nylon membrane or nitrocellulose paper (or the like). The method involves using a nucleic acid probe having a crosslinking moiety capable of forming a covalent crosslink between the nucleic acid probe and the target single-stranded DNA and performing the additional step of forming covalent bonds between the nucleic acid probe and the target DNA molecule.

An alternative embodiment of the present invention provides for a method for diagnosing a disease condition in a patient. This method also involves use of a labeled nucleic acid probe which comprises a crosslinking moiety capable of forming a covalent crosslink between the nucleic acid probe and the target nucleic acid. This method comprises the following steps: contacting a solution containing a labeled nucleic acid probe to an immobilized sample from the patient so that the labeled nucleic acid probe can hybridize to a target nucleic acid molecule indicative of a disease condition; forming a covalent bond between the nucleic acid probe and the target nucleic acid molecule; washing the immobilized biological sample to remove labeled nucleic acid probe which is not bound to the target nucleic acid molecules; and determining the amount of labeled nucleic acid probe retained at the site of the immobilized biological sample. This method may optionally further comprise, prior to the final step, the additional step of removing labeled nucleic acid probe which is not covalently bound to the target nucleic acid molecules.

In alternative embodiments, kits for carrying out the methods of the invention are also provided.

A kit for determining the presence of a target nucleic acid molecule of a biological sample comprises a nucleic acid probe having a base sequence essentially complementary to a defined region of the target nucleic acid molecule and having a crosslinking moiety which is capable of forming a covalent crosslink between the nucleic acid probe and the target nucleic acid molecule and means for removing nucleic acid probe or target which is non-specifically bound. The means for removing the excess nucleic acid will typically consist of one or more containers of prepared washing solutions. The washing solution may be water, a buffered low salt solution, a buffered high salt solution, a solution of urea, an alkaline solution, or the like. Such wash solutions are familiar to those skilled in the art.

A kit for determining the presence of a target nucleic acid molecule which is immobilized on a nylon membrane or nitrocellulose paper is also provided. This kit comprises a nucleic acid probe having a base sequence which is essentially complementary to a defined region of the target nucleic acid molecule and having a crosslinking moiety which is capable of forming a covalent crosslink between the nucleic acid probe and the target nucleic acid. The kit also comprises means for removing nucleic acid probe which is not bound to the target nucleic acid.

The kits may also optionally further comprise means of removing nucleic acid probe which is not covalently bound to the target nucleic acid molecules. A denaturing wash solution capable of disrupting hydrogen bonding between hybridized nucleic acid molecules would be a suitable means for removing nucleic acid probe which is not covalently bound to the target nucleic acid molecules. Again, such wash solutions are familiar to those skilled in the art.

In an alternative embodiment, the kits may further comprise means of labeling said nucleic acid probe.

The present invention also finds suitable use in polynucleotide or oligonucleotide array applications. In these gene chip applications, typically probes, which can either be short oligonucleotides or long amplicon products, are bound to the surface of a substrate in an arrayed pattern, and exposed to a solution containing the target DNA or RNA from the sample.

Gene chips are used primarily for sequencing-by-hybridization, gene expression profiling and single nucleotide polymorphism (SNP) typing. The sequencing-by-hybridization technique is best suited to resequencing for mutation analysis within a known gene sequence rather than the sequencing of unknown regions. For mutation and SNP analysis it is necessary to discriminate minor differences such as single nucleotide mismatches. These chips also typically use short probes from 8 to 20 bases in length. For both these reasons selectively maintaining the proper probe/target hybrids while washing away the non-specifically bound material and mismatched hybrids requires delicate adjustment of the wash stringency. Using crosslinker-containing probes eliminates these difficulties by covalently joining the probe/target hybrid together once the hybrid has formed, while still providing the capability of single-base discrimination.

The present invention provides for an array that comprises a solid support and a plurality of different nucleic acid probes immobilized on the solid support, each nucleic acid probe having a base sequence essentially complementary to a defined region of a target nucleic acid molecule and having a crosslinking moiety which is capable of forming a covalent crosslink between the nucleic acid probe and the target nucleic acid molecule.

The target nucleic acid molecule may be an animal, bacterial, fungal, human, parasitic, plant or viral nucleic acid. Other possible target sequences are listed above.

The precursor of the crosslinking moiety used on the probes of the array may be selected from the group consisting of coumarins, furocoumarins, and benzodipyrones. For instance, possibilities for the cross-linking moiety include 7-hydroxycoumarin, 6,7-dihydroxycoumarin, 6-alkoxy-7-hydroxycoumarin, psoralen, 8-methoxypsoralen, 5-methoxypsoralen, 4,5',8-trimethylpsoralen, 4'-hydroxymethyl-4,5',8-trimethylpsoralen, and 4'-aminomethyl-4,5',8-trimethylpsoralen, a haloalkyl coumarin, and a haloalkyl benzodipyrone. The U.S. patents cited above (in conjunction with the methods for determining the presence of a target nucleic acid molecule in an immobilized biological sample) disclose crosslinking compounds which would be equally suitable for use in the arrays of the invention.

Probes containing crosslinking molecules can be synthesized either directly within a specific array location on the chip, or by standard methods off the chip and then bound within a specific area to create the gene chip array. Examples of methods of producing oligonucleotide and polynucleotide arrays which are adaptable to the present invention can be found in U.S. Pat. Nos. 5,700,637 and 5,744,305, herein incorporated by reference in their entirety. The solid support material is preferably glass, silicon, or polyacrylate. However, other possibilities exist such as various metals and polymers, including conducting polymers or biopolymers.

The chip is exposed to a sample solution containing the target nucleic acid. Following hybridization under the desired stringency conditions, the chip is irradiated with UV or visible light to initiate the crosslinking reaction. Subsequently, the chip can be washed with solutions of very high stringency to remove non-specifically bound probes and other contaminants without the risk of losing the crosslinked probe/target hybrids.

Crosslinker-containing probes are reported to be able to discriminate between single-base polymorphic sites in target sequences in solution hybridization assays. (Zehnder et al., *Clinical Chemistry* 1997 43:1703–1708).

Gene expression profiling typically employs long DNA amplicons as the chipbound probe. Expressed mRNA bind to their complement within the array of probes and the strength of the signal reflects the relative amount of each mRNA and therefore the level of expression of that gene. The relative intensity maps generated illustrate the profile of genetic activity in a cell. Important to the proper evaluation of the results is the signal to noise ratio and the absence of false signals arising from non-specific adsorption of mRNA to the chip. These parameters are the same as those for immobilized nucleic acid assays. Just as crosslinker-containing probes have been demonstrated to improve in situ hybridization assays, similar gains can be made for gene chip technologies.

In addition to the arrays themselves, the present invention also provides for methods of determining the presence of a plurality of target nucleic acid molecules in a biological sample. One such method comprises the following steps: contacting the sample with the array, thereby allowing the target nucleic acid molecules to hybridize to the immobilized nucleic acid probes; forming covalent bonds between the nucleic acid probes and their hybridized target nucleic acid molecules; washing the array to remove excess nucleic acid molecules; and determining the amount and position of nucleic acid molecules which remain bound to the array. This method may also optionally include the step of removing nucleic acid molecules which are not covalently bound or are non-specifically bound to the target nucleic acid molecules.

Determining the amount and position of nucleic acid molecules can be carried out via a number of ways. For instance, the polynucleotides in a biological sample which is applied to the array could be labeled through any of the number of ways familiar to those skilled in the art. (See discussion above.) If all of the polynucleotides in the biological sample are labeled, the labeled polynucleotides remaining bound to the array at the end of the procedure can be identified as target nucleic acid molecules.

Depending upon the nature of the crosslinking moiety used in the method, the formation of the cross-link between the target nucleic acid and the nucleic acid probe may either be photochemical or chemical.

A similar method for using the invention array to diagnose a disease is also provided. A method for diagnosing a disease condition in a patient comprises first contacting a sample from a patient with the array, so that target nucleic acid molecules which are indicative of a disease condition can hybridize to the immobilized nucleic acid probes. The method also includes causing the formation of covalent bonds between the nucleic acid probes and the hybridized target nucleic acid molecules to occur. Washing the array to remove excess nucleic acid molecules is also important. As a final step, the amount and position of target nucleic acid molecules which remain bound to the array is determined.

This method may also optionally include the intermediary step of removing by stringent washing, or electric field induced desorption, nucleic acid molecules which are not covalently bound to the target nucleic acid molecules or are nonspecifically bound.

An alternative embodiment of the present invention provides for a method of determining the genotype of a patient particularly where it relates to determining which of several polymorphic sequences or nucleotides is present. An array comprised of a series of oligonucleotide probes comprising the polymorphic sequences is prepared, and the sample is contacted with the array. The method is then carried out in the same manner as above.

EXAMPLES

The following specific examples are intended to illustrate the invention and should not be construed as limiting the scope of the claims.

Example 1

In Situ Hybridization of Cells Using Crosslinker-Containing Probes.

Cells are collected from a patient and washed with phosphate-buffered saline (PBS) and pelleted at 1000 g. The cells are resuspended in PBS to a concentration of $10^6$/mL and 10 μL aliquots are spotted on slides which are then air dried. The cells are fixed in 4% paraformaldehyde for 20 minutes at room temperature and rinsed once with water. The cells are dehydrated with sequential immersion in 70%, 80%, and 100% ethanol and air dried.

The immobilized cells are treated with proteinase K in PBS at 37° C. for 20 minutes and rinsed with water. The cells are then treated with acetic anhydride in 0.1 M triethanolamine (pH 8) for 10 minutes at room temperature and rinsed with water. The cells are dehydrated in ethanol, as above, and then the nucleic acids are denatured by treatment with 90% formamide in 0.1×sodium saline citrate (SSC) for 15 minutes at 65° C. The cells are rinsed with water and again dehydrated with ethanol.

Hybridization is performed with the crosslinker-containing DNA probes in 20% formamide, 2×SSC, 10% dextran sulphate, 20 mM HEPES, pH 7.4, 1×Denhardt's solution, 200 μg/mL calf-thymus DNA for one hour at 37° C. The slides are washed briefly with 2×SSC and 0.05% Tween™ at 37° C. and then irradiated with a UV light source (300–370 nm) for 15 minutes at 37° C. Post-crosslinking washing is done three times for fifteen minutes each with 2×SSC/0.05% Tween 20 at 60° C.

To detect the crosslinked hybrids, the immobilized cells are equilibrated in 0.1 M Tris (pH 7.4), 0.15 M NaCl, 0.05% Tween 20 (TNT) for five minutes at room temperature and then blocked with 0.1 M Tris (pH 7.4), 0.15 M NaCl containing 0.05% blocking reagent for 45 minutes at room temperature. Bound hybrids are labeled with 200 μL antifluorescein-horseradish peroxidase (HRP) in a 30 minute incubation at room temperature, washed four times with TNT at room temperature, and then incubated with 120 μL biotinyl tyramide for 10 minutes at room temperature. The slides are washed four times in TNT, incubated with SA-HRP at room temperature for 30 minutes and washed 4 times with TNT, incubated with 120 μL Cy3-tyramide for 10 minutes at room temperature, and again washed in TNT. The cells are counter-stained with 5μ/mL DAPI, mounted with Vectashield®, and visualized under a fluorescent microscope equipped with the necessary excitation and emission filters for the fluorophore and counterstain.

Example 2

Detection of Human Papillomavirus Type 16 in Cells

In situ hybridization experiments were undertaken to demonstrate the utility of crosslinkable probes. The target organism was human papillomavirus type 16. The probe sequences are sequence ID Numbers 1–14 of Table 1. Two types of cell lines were used in the experiments, CaSki cells, and C-33 cells. CaSki cells contain ~500 copies of the viral genome, whereas C-33 cells do not contain the viral genome and were used as negative controls.

Each cell type was mounted on slides and treated to the same pretreatment and hybridization protocol as detailed in Example 1, above. Some samples of each cell type were then irradiated with UV light to initiate the crosslinking reaction as described above, while other samples were incubated without being exposed to UV light. Subsequently, all samples were treated to the same washing and detection protocol detailed in Example 1, above.

Figure 1A:
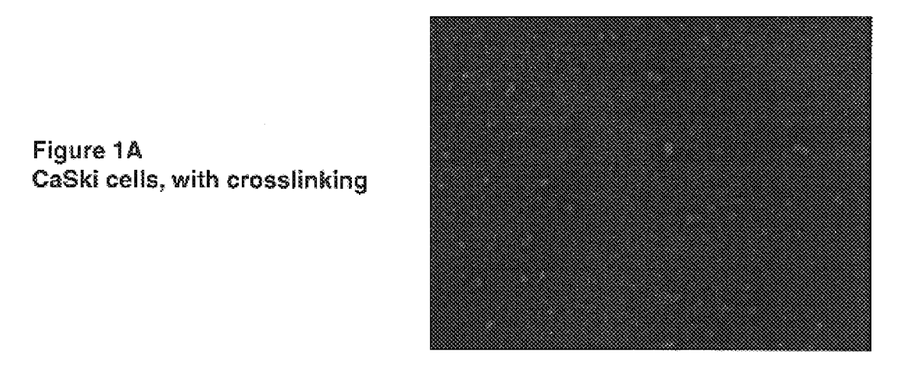
FIGS. 1a–1c show cells which have been assayed by in situ hybridization for the presence of human papillomavirus with a probe that contains a crosslinking moiety, with and without UV irradiation to induce crosslink formation.
Figure 1B:
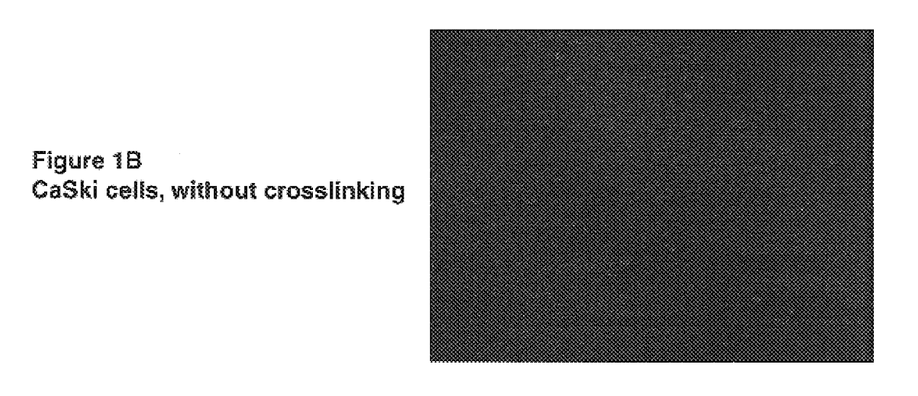
Figure 1C:
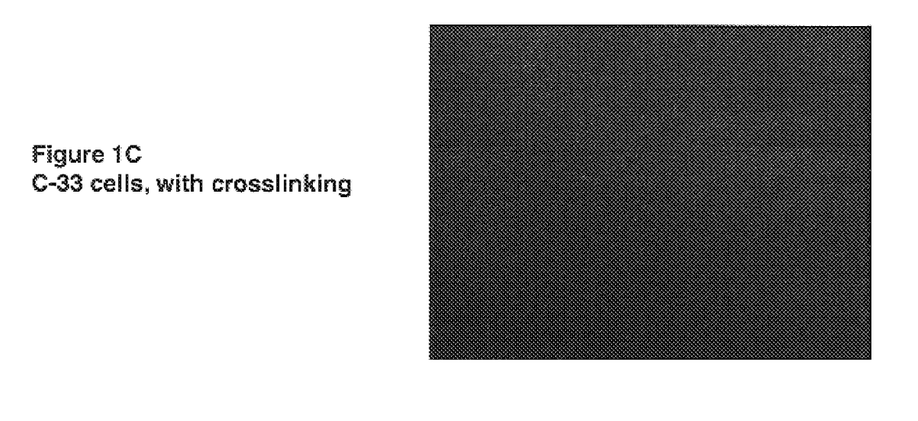

The images of FIG. 1 illustrate the results of the experiments. The images represent the fluorescent emission from the dye Cy-3, which has been deposited via an indirect detection procedure for antigen-labeled oligonucleotide probes specific for HPV 16. FIG. 1a shows the CaSki cells, with crosslinking, under low power magnification. FIG. 1b shows the CaSki cells, without crosslinking, under low power magnification. FIG. 1c shows the C-33 cells, with crosslinking, under low power magnification.

The hybridization procedure has clearly distinguished between cells which contain the human papillomavirus. (FIGS. 1a and 1b) and cells which do not (FIG. 1c). The imaging threshold in the image of FIG. 1c was adjusted to a low value in order to find any low level of signal, and only a homogeneous background signal was observed. FIG. 1a indicates that in the cells containing human papillomavirus, the probes specifically localize in the nucleus and provide a strong signal.

The difference in the intensity of the signal between FIG. 1a (crosslinked probe) and FIG. 1b (no crosslinking) is clearly evident. With crosslinking, the probe/target hybrids are retained and therefore contribute to signal generation, whereas without crosslinking the hybrids are washed apart and are not present to contribute to signal generation.

Image analysis of such slides in a similar experiment revealed a difference in integrated signal intensity of more than an order of magnitude.

Example 3

In Situ Hybridization of a Tissue Section Using Crosslinker-Containing Probes.

If the sample type is a tissue section, thin (5 μm) tissue sections are first cut from paraffin-embedded tissue blocks and then placed on glass slides. The embedded tissue is dewaxed by two five minute immersions in xylene, washed twice in 100% ethanol, and airdried. After this, the assay procedure is the same as for cell-based in situ hybridization, starting from the paraformaldehyde fixing step (see Example 1, above).

Example 4

In Situ Hybridization Assay for Human Papillomavirus 16 DNA in Clinical Specimens Pap smear samples from two patients were collected, and placed into a buffered methanol solution (PreserveCyt™ solution, from CYTYC Corporation). Several drops of this solution were spotted onto poly-L-lysine coated slides (Newcomer Supply) and left to dry.

The immobilized cells were treated with pepsin (50 ug/mL) in 20 mM HCl at 37° C. for 20 minutes and then rinsed with water. The assay procedure given in Example 1 was then followed. The assay was performed with 17 nucleic acid probes, sequence ID numbers 1, 3, 4, 5, 6, 7, 8, 9, 12, 14, 15, 16, 17, 18, 19, 20 and 21, using 10 pmol of total probe amount (0.588 pmol of each probe) per assay.

Examination of the assays using fluorescence microscopy indicated sample 1 was positive for HPV 16 DNA and sample 2 was negative.

Cells from the same patient samples not fixed on slides were also tested for HPV 16 using a PCR procedure. The results from the PCR tests correlated with the results obtained by the in situ hybridization assay.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

TABLE 1

Human Papillomavirus Type 16
Probes complementary to sequences within the E6 and E7 genes
Probes for Example 2: 1–14
Probes for Example 4: 1,3,4,5,6,7,8,9,12,14,15,16,17,18,19,20,21

| Probe and SEQ ID No. | Sequence |
| --- | --- |
| 1 | 3'-GTGGTTTTCTCTTGACGTTACAXAF |
| 2 | 3'-GGTGTCCTCGCTGGGTCTTTCAXTF |
| 3 | 3'-AXATTATAATCTTACACACATGACF |
| 4 | 3'-TATACGACATACACTATTTACAXAF |
| 5 | 3'-AXAATAAGATTTTAATCACTCATAF |
| 6 | 3'-TXATCTTGTCGTTATGTTGTTTGGF |
| 7 | 3'-AXACAATTAATCCACATAATTGACF |
| 8 | 3'-AXACAGGACTTCTTTTCGTTTCTGF |
| 9 | 3'-AXACCTGTTTTTCGTTTCTAAGGTF |
| 10 | 3'-TACGTACCTCTATGTGGATGTXAF |
| 11 | 3'-TAXATACAATCTAAACGTTGGTCTCF |
| 12 | 3'-TTCGTCTTGGCCTGTCTCGGGTXAF |
| 13 | 3'-GAXATGCGAAGCCAACACGCATGTTF |
| 14 | 3'-GTGTGTGCATCTGTAAGCATGAXAF |
| 15 | 3'-AXTACGTGTCTCGACGTTTGTTGAF |
| 16 | 3'-GACGCAGCACTCCATATACTGAXAF |
| 17 | 3'-AXAGCCCTAAATACGTATCATATAF |
| 18 | 3'-TXATAACAATATCAAACATACCTTF |
| 19 | 3'-AXATTCCCCAGCCACCTGGCCAGCF |
| 20 | 3'-AXAACAACGTCTAGTAGTTCTTGAF |
| 21 | 3'-TXACATTGGAAAACAACGTTCACAF |

X = crosslinker = 3-O-(7-coumarinyl)glycerol
F = fluorescein

We claim:

1. A kit for determining the presence of a target nucleic acid molecule of an immobilized biological sample, comprising:

a nucleic acid probe having a complementary base sequence to a defined region of the target nucleic acid molecule and having a crosslinking moiety which is capable of forming a covalent crosslink between the nucleic probe and the target nucleic acid, wherein the probe is SEQ ID NO:14, optionally having a marker other than a fluorescein molecule; and means for removing nucleic acid probe which is not bound to the target nucleic acid molecule.

2. The kit of claim 1, further comprising means of removing nucleic acid probe which is not covalently bound to the target nucleic acid molecule.

3. The kit of claim 1, further comprising means of labeling said nucleic acid probe.

4. An array, comprising:

a solid support; and a plurality of different nucleic acid probes immobilized on said solid support, each nucleic acid probe having a base sequence complementary to a defined region of a target nucleic acid molecule and having a crosslinking moiety which is capable of forming covalent crosslink between the nucleic acid probe and the target nucleic acid molecule, wherein one of the probes is SEQ ID NO: 14, optionally having a marker other than a fluorscein molecule.

5. The array of claim 4, wherein at least one of the nucleic acid probes is complementary to a target nucleic acid molecule selected from the group consisting of animal, bacterial, fungal, human, parasitic, plant and viral nucleic acids.

6. The array of claim 4, wherein said crosslinking moiety is selected from the group consisting of coumarins, furocoumarins and benzodipyrones.

7. The array of claim 4, wherein the crosslinking moiety is selected from the group consisting of coumarin, 7-hydroxycoumarin, 6,7-hydroxycoumarin, 6,7-dihydroxycoumarin, 6-alkoxy-7-hydroxycoumarin, psoralen, 8-methoxypsoralen, 5-methoxypsoralen, 4, 5',8-trimethylpsoralen, 4'-hydroxymethyl-4,5',8-trimethylpsoralen, and 4'-aminomethyl-4,5',8-trimethylpsoralen, a haloalkyl coumarin, a haloalkyl furocoumarin and a haloalkyl benzodipyrone.

8. The array of claim 4, wherein the crosslinking moiety is a mono-adducted furocoumarin:nucleoside adduct.

9. A method for determining the presence of a plurality of target nucleic acid molecules in a biological sample, comprising:
   (a) contacting the sample with the array of claim 4, wherein the target nucleic acid molecules hybridize to the immobilized nucleic acid probes;
   (b) forming covalent bonds between the nucleic acid probes and their hybridized target nucleic acid molecules;
   (c) washing the array to remove excess nucleic acid molecules; and
   (d) determining the amount and position of nucleic acid molecules which remain bound to the array.

10. The method of claim 9, further comprising the step of washing the array to remove non-specifically bound nucleic acid molecules.

11. The method of claim 9, further comprising the step of applying an electric field across the substrate to desorb nonspecifically bound nucleic acid molecules.

12. The method of claim 9, further comprising the step of disrupting nucleic acid hybridization within the immobilized biological sample.

13. The method of claim 9, wherein the formation of the covalent bond occurs photochemically.

14. The method of claim 9, wherein the formation of the covalent bond occurs chemically.

15. A method for diagnosing a disease condition in a patient, comprising:
   (a) contacting a sample from a patient with the array of claim 4, so that target nucleic acid molecules which are indicative of a disease condition can hybridize to the immobilized nucleic acid probes;
   (b) forming covalent bonds between the nucleic acid probes and the hybridized target nucleic acid molecules;
   (c) washing the array to remove nonspecifically bound nucleic acid molecules; and
   (d) determining the amount and position of target nucleic acid molecules which remain bound to the array.

16. The method of claim 15, further comprising the step of removing nucleic acid molecules which are not covalently bound to the target nucleic acid molecules, prior to the final step.

* * * * *

SEQUENCE LISTING

<160> NUMBER OF SEQ ID NOS: 21

<210> SEQ ID NO 1
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (1)..(2)
<223> OTHER INFORMATION: 3-O-(7-coumarinyl)-glycerol between position 1
      and 2

<400> SEQUENCE: 1
aacattgcag ttctcttttg gtg                                           23

<210> SEQ ID NO 2
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature

```
<222> LOCATION: (1)..(2)
<223> OTHER INFORMATION: 3-O-(7-coumarinyl)-glycerol between position 1
      and 2

<400> SEQUENCE: 2
tactttctgg gtcgctcctg tgg                                            23

<210> SEQ ID NO 3
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 3
cagtacacac attctaatat taa                                            23

<210> SEQ ID NO 4
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (1)..(2)
<223> OTHER INFORMATION: 3-O-(7-coumarinyl)-glycerol between position 1
      and 2

<400> SEQUENCE: 4
aacatttatc acatacagca tat                                            23

<210> SEQ ID NO 5
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 5
atactcacta attttagaat aaa                                            23

<210> SEQ ID NO 6
```

```
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 6
ggtttgttgt attgctgttc tat                                            23

<210> SEQ ID NO 7
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 7
cagttaatac acctaattaa caa                                            23

<210> SEQ ID NO 8
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 8
gtctttgctt ttcttcagga caa                                            23

<210> SEQ ID NO 9
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
```

```
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 9
tggaatcttt gcttttttgtc caa                                              23

<210> SEQ ID NO 10
<211> LENGTH: 22
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(22)
<223> OTHER INFORMATION: chemically synthesized or biologically prepared
      nucleic acid probe
<221> NAME/KEY: misc_feature
<222> LOCATION: (1)..(2)
<223> OTHER INFORMATION: 3-O-(7-coumarinyl)-glycerol between position 1
      and 2

<400> SEQUENCE: 10
atgtaggtgt atctccatgc at                                                22

<210> SEQ ID NO 11
<211> LENGTH: 24
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(24)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 11
ctctggttgc aaatctaaca taat                                              24

<210> SEQ ID NO 12
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (1)..(2)
<223> OTHER INFORMATION: 3-O-(7-coumarinyl)-glycerol between position 1
      and 2

<400> SEQUENCE: 12
atgggctctg tccggttctg ctt                                               23
```

<210> SEQ ID NO 13
<211> LENGTH: 24
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(24)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 13
ttgtacgcac aaccgaagcg taag                                    24

<210> SEQ ID NO 14
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (1)..(2)
<223> OTHER INFORMATION: 3-O-(7-coumarinyl)-glycerol between position 1
      and 2

<400> SEQUENCE: 14
aagtacgaat gtctacgtgt gtg                                     23

<210> SEQ ID NO 15
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 15
agttgtttgc agctctgtgc ata                                     23

<210> SEQ ID NO 16
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)

```
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (1)..(2)
<223> OTHER INFORMATION: 3-O-(7-coumarinyl)-glycerol between position 1
      and 2

<400> SEQUENCE: 16
aagtcatata cctcacgacg cag                                          23

<210> SEQ ID NO 17
<211> LENGTH: 24
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(24)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 17
atatactatg cataaatccc gcaa                                         24

<210> SEQ ID NO 18
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 18
ttccatacaa actataacaa tat                                          23

<210> SEQ ID NO 19
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23
```

-continued

```
<400> SEQUENCE: 19
cgaccggtcc accgacccct taa                                              23

<210> SEQ ID NO 20
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 20
agttcttgat gatctgcaac aaa                                              23

<210> SEQ ID NO 21
<211> LENGTH: 23
<212> TYPE: DNA
<213> ORGANISM: Artificial Sequence
<220> FEATURE:
<223> OTHER INFORMATION: nucleic acid probe
<221> NAME/KEY: misc_feature
<222> LOCATION: (1)..(1)
<223> OTHER INFORMATION: fluorescein attached at 5' end
<221> NAME/KEY: source
<222> LOCATION: (1)..(23)
<223> OTHER INFORMATION: chemically synthesized or biologically prepared
      nucleic acid probe
<221> NAME/KEY: misc_feature
<222> LOCATION: (22)..(23)
<223> OTHER INFORMATION: 3-O-(7-coumarinyl)-glycerol between position 22
      and 23

<400> SEQUENCE: 21
acacttgcaa caaaaggtta cat                                              23
```